United States Patent [19]
Parel et al.

[11] Patent Number: 5,098,443
[45] Date of Patent: Mar. 24, 1992

[54] METHOD OF IMPLANTING INTRAOCULAR AND INTRAORBITAL IMPLANTABLE DEVICES FOR THE CONTROLLED RELEASE OF PHARMACOLOGICAL AGENTS

[75] Inventors: Jean-Marie Parel; Richard Parrish; Lourdes Portugal; Karl R. Olsen, all of Miami, Fla.

[73] Assignee: University of Miami, Miami, Fla.

[21] Appl. No.: 651,543

[22] Filed: Feb. 6, 1991

Related U.S. Application Data

[62] Division of Ser. No. 327,989, Mar. 23, 1989, abandoned.

[51] Int. Cl.⁵ .............................................. A61F 2/14
[52] U.S. Cl. ......................................... 623/4; 424/428; 604/294; 604/890.1
[58] Field of Search ................. 623/4, 5, 6; 604/294, 604/890.1, 891.1, 892.1; 424/426, 427, 428, 429

[56] References Cited
U.S. PATENT DOCUMENTS 3,995,635 12/1976 Higuchi .
4,439,198 3/1984 Brightman et al. ................. 424/426
4,519,801 5/1985 Edgren ................................ 424/427
4,573,998 3/1986 Mazzocco .......................... 606/107
4,713,072 12/1987 Bowald ................................. 623/6
4,731,080 3/1988 Galin ................................... 623/66
4,863,457 9/1989 Lee .
4,919,130 4/1990 Stoy et al. ......................... 606/107

FOREIGN PATENT DOCUMENTS 1529143 10/1978 United Kingdom .

*Primary Examiner*—Randy C. Shay
*Attorney, Agent, or Firm*—Cushman, Darby & Cushman

[57] ABSTRACT

A series of implants for intraocular and/or intraorbital use are provided which permit the controlled release of pharmacological agents. The implants are substantial C-shaped rings and are insertable through incisions made in the eye wall or are sutured around the globe of the eye. The C-shaped rings may be formed from the biodegradable polymers so as to release a drug as the polymer biodegrades or the implant may be in the form of a hollow flexible polymeric cocoon with the drug disposed therewithin for slow release by osmosis.

16 Claims, 4 Drawing Sheets

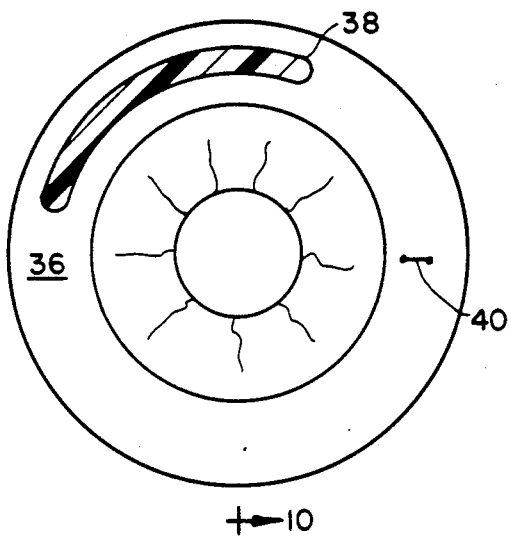
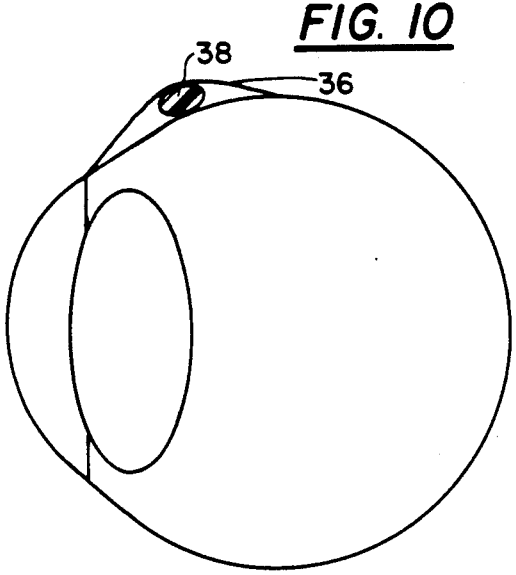
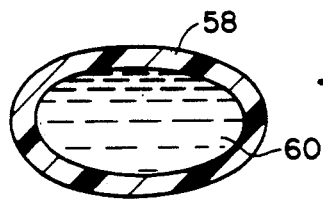
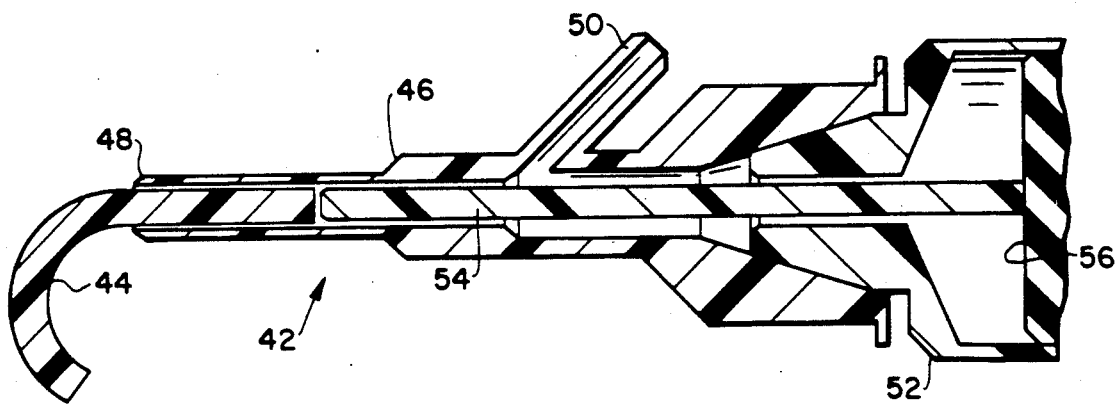

METHOD OF IMPLANTING INTRAOCULAR AND INTRAORBITAL IMPLANTABLE DEVICES FOR THE CONTROLLED RELEASE OF PHARMACOLOGICAL AGENTS

This is a division of application Ser. No. 07/327,989, filed Mar. 23, 1989, now abandoned.

BACKGROUND OF THE INVENTION

1. Field of the Invention

The present invention relates to a device and method for intraocular or intraorbital controlled release of pharmacological agents.

2. Description of the Related Art

A number of devices have been proposed which permit controlled release of pharmacological agents to various parts of the body and have facilitated dramatic advances in the medical field. Indeed, slow release of insulin from such devices can eliminate the need for repeated insulin injections in the case of a diabetic and the slow release of bactericides can minimize the likelihood of post-operative infection in other cases.

The controlled release of agents for intraocular or intraorbital use would allow optimized therapeutics for AIDS (CMV retinitis), for endophthalmitis (prevention of/cure of bacterial, viral or fungal infections), in proliferative diseases (such as proliferative vitreoretinopathy [PVR], lens epithelium proliferation (secondary cataract), for malignant intraocular tumors and other diseases. In addition, intraorbitally, such a technique would allow control of wound healing (e.g., reduction of scarred tissue volume in glaucoma filtration surgery, retinal detachment surgery (scleral buckling procedure), and strabismus surgery). However to date, devices for the controlled release of appropriate agents for intraocular or intraorbital use have not been developed.

It would therefore be desirable to provide a device for intraocular or intraorbital use which permits the controlled release or slow release of pharmacological agents.

SUMMARY OF THE INVENTION

The present invention provides a series of devices or implants for intraocular or intraorbital use which permit the controlled release of pharmacological agents. The devices provided in accordance with the present invention are substantially "C"-shaped rings and are flexible for insertion through small incisions made in the eye wall or are sutured around the globe. The devices provided in accordance with the present invention are designed to conform with existing surgical techniques (vitrectomy, cataract surgery, penetrating keratoplasty, scleral buckling procedures and glaucoma and strabismus surgery). The implant releases the selected pharmacological agents via biodegradation or by osmosis. The released drug then reaches targeted tissue by diffusion.

BRIEF DESCRIPTION OF THE DRAWINGS

FIG. 9 is a front elevational view showing yet another implant location for the device of the invention;

FIG. 10 is a view taken along line 10—10 of FIG. 9;

FIG. 11 is a cross-sectional view of a device in accordance with one embodiment of the present invention; and FIG. 12 is a cross-sectional view showing an implant inserter provided in accordance with the present design.

DETAILED DESCRIPTION OF THE PRESENTLY PREFERRED EXEMPLARY EMBODIMENT

Figure 1:
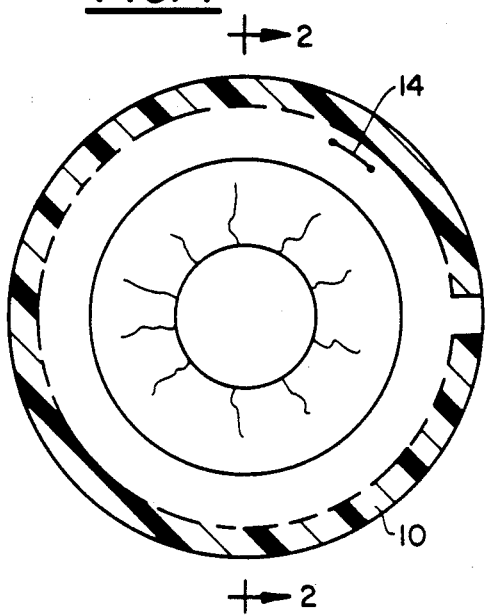
FIG. 1 is a schematic front elevational view showing an implant provided in accordance with the present invention within the vitreous cavity.
Figure 2:
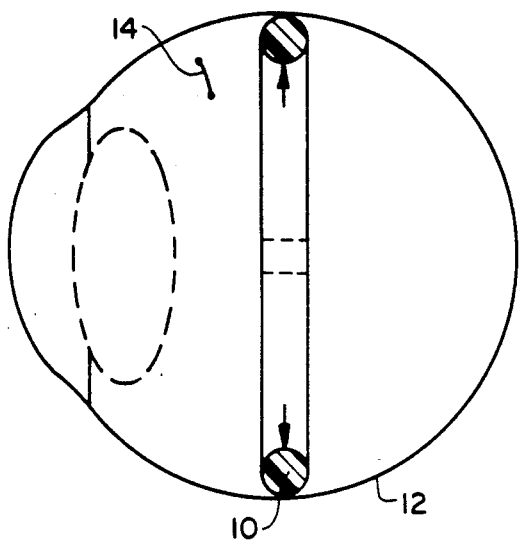
FIG. 2 is a view taken along line 2—2 of FIG. 1.

Referring to the drawings, the implant of the invention is shown disposed at various locations in and about a patient's eye. Each disposition of the implant is selected to facilitate optimal drug delivery for the particular treatment being effected and the contemporaneous surgical procedure. For example, referring to FIGS. 1 and 2, intravitreally positioning the "C" ring implant 10 at the equator of the globe 12 is ideal for drug release in the vitreous cavity following vitreoretinal surgery. The implant 10 can be inserted through an incision as at 14 and is preferably preformed so as to have a diameter slightly larger than the diameter of the vitreous cavity 12. Once inserted, then, the implant 10 will not encroach upon the visual axis and will be maintained in position initially by its resiliency and, within two to four weeks, probably by encapsulation. This device could also be utilized in the treatment of ocular malignancy when loaded with appropriate antimitotic agents such as but not limited to 5-fluorouracil, daunomycin, and others, and for the treatment of CMV retinitis in AIDS patients when loaded with ganciclovir.

Figure 3:
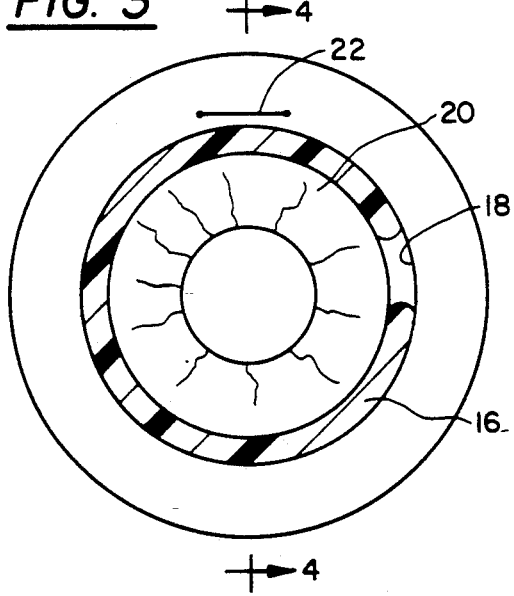
FIG. 3 is a front elevational view showing an alternate size and location for an implant located in the eye's anterior chamber provided in accordance with the present invention.
Figure 4:
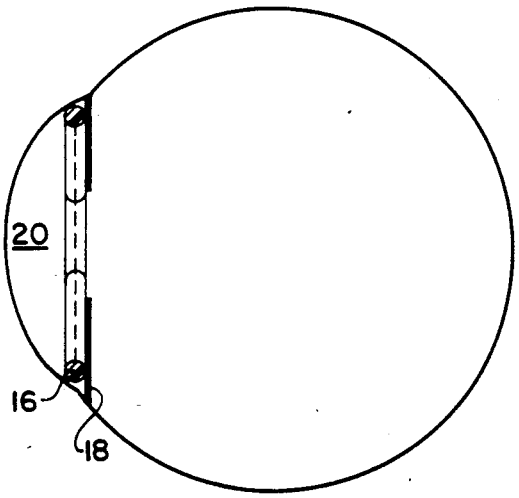
FIG. 4 is a view taken along line 4—4 of FIG. 3.

Referring to FIGS. 3 and 4, a smaller "C" ring 16 can be made to fit into the angle 18 of the anterior segment 20 following penetrating keratoplasty (corneal transplantation), intraocular cataract surgery, vitrectomy, glaucoma filtering surgery, etc. Again, the implant can be inserted through the surgical incision 22 and could be provided for releasing antibiotics, antimicotics, antimitotics, and/or growth factors.

Figure 5:
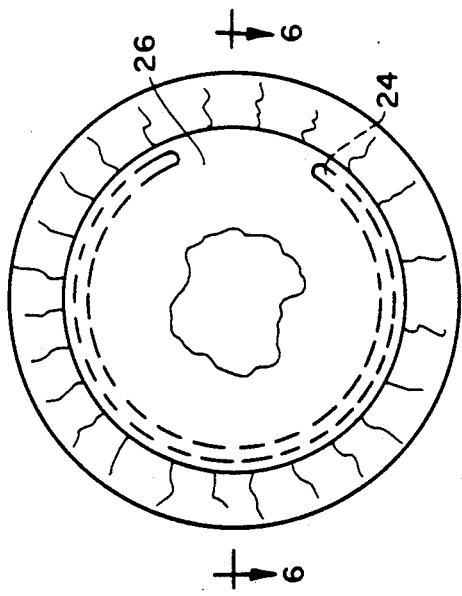
FIG. 5 is a front elevational view showing the implant of the invention disposed at the equator of the lens capsular bag.
Figure 6:
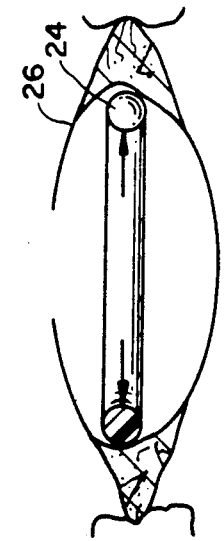
FIG. 6 is a view taken along line 6—6 of FIG. 5.

Referring to FIGS. 5 and 6, another location for a "C" ring 24 provided in accordance with the present invention is at the equator of the lens capsular bag 26. Such a "C" ring 24 can be introduced during extracapsular cataract procedures, after removal of nucleus and cortex, to release drugs preventing lens epithelium proliferation, the cause of posterior capsule opacification (secondary cataract). In the alternative, the "C" ring of the invention could be used as an element for intraocular lens (IOL) construction or as an IOL coating.

Figure 7:
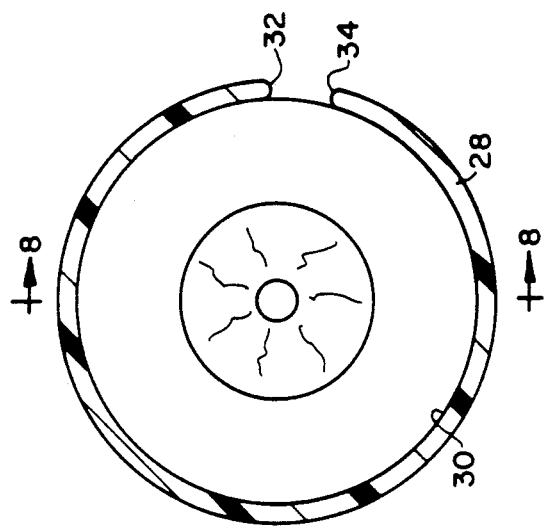
FIG. 7 is a front elevational view showing an alternate location and configuration of the implant provided in accordance with the present invention.
Figure 8:
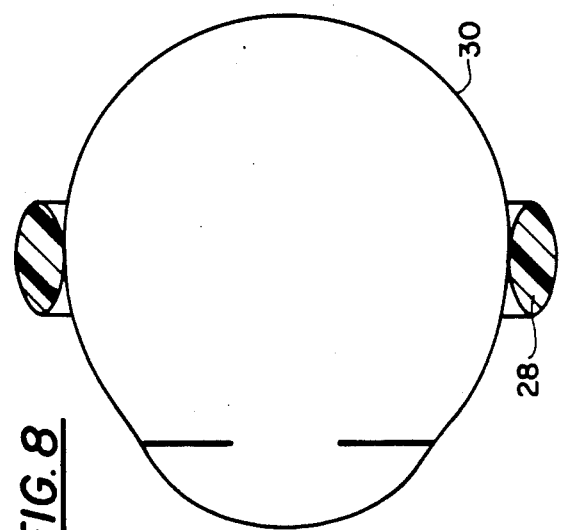
FIG. 8 is a view taken along line 8—8 of FIG. 7.
Figure 8A:
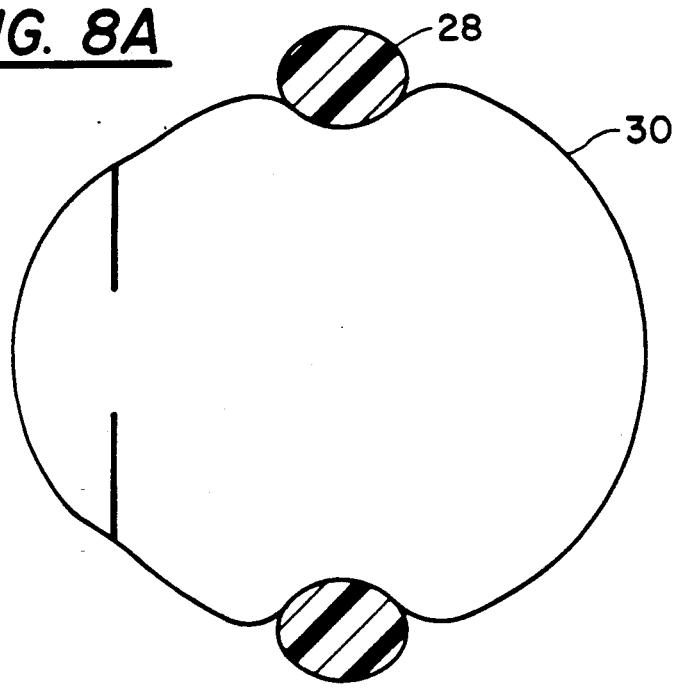
FIG. 8A is a view similar to FIG. 8 showing the eye wall deformation when the buckle compresses the eye's equator.
Figure 8B:
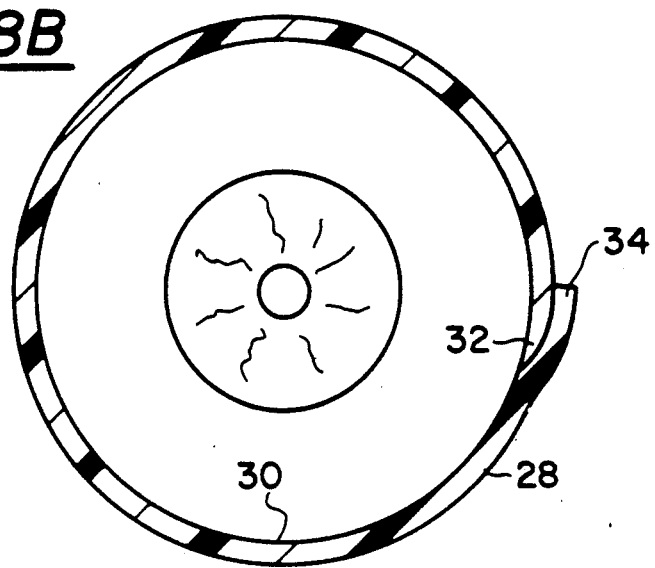
FIG. 8B is a front elevational view showing an alternate location and configuration of the implant provided in accordance with the present invention.

By modifying the ring design slightly as, shown in FIGS. 7 and 8, the "C" ring 28 can be used in the orbit external to the globe 30 (as a buckle) and provide therapeutic drug release to the orbital tissue, ocular muscles, the sclera, and, by diffusion, into intraocular tissues. The ends 32, 34 of ring 28 could be made to overlap (FIG. 8B) or butt and serve as a temporary or permanent buckle (elastic band used in retinal detachment surgery). In the alternative, as shown in FIG. 8A, the ring 28 could be molded to have a diameter slightly less than the diameter of the globe 30 so that the resiliency of the ring tends to clamp it about the globe and deforming it as for conventional scleral buckling procedure performed with silicone elastic bands wherein the buckle compasses the eye's equator bringing the eye tissue outer coat (sclera) into contact with the detached retina (inner coat). The ring can also be sutured about the globe to ensure retention of the ring in an appropriate position.

Even further, as shown in FIGS. 9 and 10, positioned under the conjunctiva 36 the "C" ring 38 can release antimitotic agents in order to modulate would healing and prevent early closure of the filtering bleb in glaucoma surgery and minimize scarring during strabismus and retinal reattachment procedures.

Intraocular insertion of the flexible "C" rings described above can be accomplished by injection with a simple surgical instrument during the contemporaneous procedure (e.g.; vitrectomy, cataract surgery, penetrating keratoplasty, glaucoma filtering surgery) through a small incision made in the eye wall through the conjunctiva as shown, for example, at 14, 22, and 40.

Referring to FIG. 12, one embodiment of an instrument 42 for implanting the device 44 which includes a cannula 46 for receiving the implant 44 in a straightened configuration. The cannula 46 preferably has a beveled forward end 48 for facilitating insertion of the same into an incision in the eye wall. The cannula 46 further preferably includes a side arm structure 50 for enabling infusion and/or irrigation and aspiration of materials. A modified syringe structure 52 having a piston 54 extending forwardly from the plunger 56 can be employed to eject the implant 44 from the cannula.

In one form of the present invention, the device substrate is made from synthetic biodegradable polymers. The drug is mixed with the polymer (both in fine powder form or with the drug in fine powder form and the polymer in the liquid state) and processed into a "C" ring-shaped implant by solvent casting or by thermoforming through compression or injection molding techniques. Biodegradation of the polymer releases the drug. For a given application site (e.g. intraocular, intraorbital, etc.) release time is a function of the polymer and implant shape selected and can be made to vary from about one week to about one year.

In another form, the drug is covalently bonded to the polymer backbone via water soluble or hydrolyzable organic links (e.g.: peptides). Drug release occurs by biodegradation of these links.

In yet another form of the invention, covalent bonds are formed between the polymer and drug molecules to create a polymeric drug system. Polymeric degradation releases the drug.

In a fourth form, the drug is contained in a hollowed flexible polymeric cocoon 58 shaped as a "C" ring (FIG. 11). The drug 60 diffuses through the wall of the ring into tissue via osmosis.

Biodegradable polymers have been tested subconjunctivally, intraorbitally and intraocularly both in the anterior and the posterior (vitreous cavity) chambers.

Twenty-six of 140 biopolymers tested were found to have adequate physical properties for the fabrication of ocular implants. Three were found intraocularly biocompatible and two of these were selected for the fabrication of implants. Using a 10/90 lactide-glycolide copolymer, biodegradable retinal fixation tacks (biopins) were fabricated and implanted in a series of 30 rabbits. In vitrectomized and non-vitrectomized eyes, the biopins fully biodegraded at 8 and 12 months respectively. As with their metallic counterparts, encapsulation of the biopins develops at approximately 1 month. No foreign body or toxic reaction was observed histologically.

A biodegradable polymer controlled drug release matrix containing 10% 5-FU has been fabricated and tested in vitro. More particularly, using a 50/50 lactide-glycolide copolymer, a 10% 5-FU controlled drug released matrix designed for rapid release was developed. An in vitro technique was developed to assess the pharmacokinetics of the matrix.

Using a 10/90 lactide-glycolide compound, each biopin was designed to release 10 ng of drug per hour over a 4 month period. An increased drug rate of 10 ug/hr can be achieved with a "C ring" implant. Injectable through a 20 ga pars plana incision, this larger implant can be designed to fit the retinal equator thereby avoiding retinal perforation.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed is:

1. A method of implanting a device into an eye for the controlled release of intraocular and intraorbital pharmacological agents comprising:

providing an implant having at least one pharmacological agent one of incorporated and encapsulated therewithin;

providing an inserter including a cannula having a first end and second end and a passage defined therethrough from said first end to said second end;

mounting a syringe to said first end of said cannula, said syringe including a plunger and a piston extending forwardly therefrom into said passage of said cannula;

mounting said implant within said passage forwardly of said piston whereby movement of said piston relative to said cannula ejects said implant from said cannula;

inserting said cannula into an incision in the eye; and ejecting said implant from said cannula;

whereby said pharmacological agent is gradually released from said implant to the eye.

2. A method of implanting a device into an eye for the controlled release of intraocular and intraorbital pharmacological agents comprising:

providing an inserter including a cannula having a first end and second end and a passage defined therethrough from said first end to said second end;

mounting a syringe to said first end of said cannula, said syringe including a plunger and a piston extending forwardly therefrom into said passage of said cannula;

mounting an implant within said passage forwardly of said piston whereby movement of said piston relative to said cannula ejects said implant from said cannula;

inserting said cannula into an incision in the eye; and ejecting said implant from said cannula, the implant being inserted so as to be positioned intravitreally at the eye's equator so as to release said pharmacological agent into the eye's vitreous cavity.

3. A method as in claim 1, wherein the implant is inserted so as to be disposed in an angle defined by the intersection of the eye's iris and cornea.

4. A method as in claim 1, wherein the implant is inserted so as to be disposed at an equator of the eye's lens capsular bag.

5. A method as in claim 4, wherein the implant is introduced during an extracapsular procedure after removal of the eye's lens nucleus and cortex to release pharmacological agents for preventing lens epithelium proliferation.

6. A method as in claim 1, wherein the implant is positioned radially inwardly of the conjunctiva and releases antimitotic and/or other pharmacological agents.

7. A method as in claim 1, wherein said step of mounting the implant comprises mounting an implantable device formed from a biodegradable polymer having a drug incorporated therein so that the biodegradation of the polymer releases the drug.

8. A method as in claim 7, wherein said steps of providing an implant, mounting said implant and ejecting said implant comprise providing, mounting and ejecting an implantable device which is substantially C-shaped once implanted.

9. A method as in claim 1, wherein said step of mounting an implantable device comprises mounting a hollow flexible polymeric cocoon having a drug disposed interiorly of said polymeric cocoon, said drug being diffusible through the walls of said polymeric cocoon into tissue via osmosis.

10. A method of implanting a device into an eye for the controlled release of intraocular and intraorbital pharmacological agents comprising:

providing an inserter including a cannula having a first end and second end and a passage defined therethrough from said first end to said second end;

mounting a syringe to said first end of said cannula, said syringe including a plunger and a piston extending forwardly therefrom into said passage of said cannula;

mounting an implant within said passage forwardly of said piston whereby movement of said piston relative to said cannula ejects said implant from said cannula;

inserting said cannula into an incision in the eye; and ejecting said implant from said cannula, the implant being disposed in surrounding relation to the exterior of the eye to provide therapeutic pharmacological agent release to orbital tissue, ocular muscles, sclera, and by diffusion into intraocular tissues.

11. A method as in claim 10, wherein the implant is sized so that first and second ends thereof overlap to serve as a buckle structure.

12. A method of controllably releasing intraocular and intraorbital pharmacological agents into an eye comprising:

making an implantable device for the controlled intraocular and intraorbital release of pharmacological agents, including providing a biodegradable polymer having a drug incorporated therein and forming said polymer into a C-shaped ring, providing an inserter including a cannula having a first end and second end and a passage defined therethrough from said first end to said second end;

mounting a syringe to said first end of said cannula, said syringe including a plunger and a piston extending forwardly therefrom into said passage of said cannula;

mounting said C-shaped ring within said passage forwardly of said piston whereby movement of said piston relative to said cannula ejects said C-shaped ring from said cannula;

inserting said cannula into an incision in the eye; and ejecting said implant from said cannula;

whereby said pharmacological agent is gradually released from said implant to the eye.

13. A method as in claim 12, wherein said step of making further includes the steps of:

providing a drug to be delivered by the implantable device in powder form;

providing a polymer for forming the device in one of powder form and liquid form;

mixing the powder drug and polymer; and processing said mixture into a C-ring shaped implant by one of solvent casting and thermal forming through one of compression and injection molding techniques.

14. A method as in claim 12, further comprising the steps of covalently bonding the drug to a polymer backbone for the implant via water soluble or hydrolyzable organic links whereby release of the drug occurs by a biodegradation of said organic links.

15. A method as in claim 12, further comprising forming covalent bonds between the polymer and drug molecules so as to create a polymeric drug system such that polymeric degradation releases the drug.

16. A method of controllably releasing intraocular and intraorbital pharmacological agents into an eye comprising:

forming an implantable device including forming a hollow flexible polymeric cocoon shaped as a C-ring and filling said polymeric cocoon with a pharmacological agent which is diffusible through the wall of said polymeric cocoon by osmosis;

providing an inserter including a cannula having a first end and second end and a passage defined therethrough from said first end to said second end;

mounting a syringe to said first end of said cannula; said syringe including a plunger and a piston extending forwardly therefrom into said passage of said cannula;

mounting said C-shaped ring within said passage forwardly of said piston whereby movement of said piston relative to said cannula ejects said C-shaped ring from said cannula;

inserting said cannula into an incision in the eye; and ejecting said implant from said cannula;

whereby said pharmacological agent is gradually released from said implant to the eye.

* * * * *